United States Patent

Swain et al.

[11] Patent Number: 5,792,153
[45] Date of Patent: Aug. 11, 1998

[54] SEWING DEVICE

[75] Inventors: Paul Swain; Feng Gong; Geoffrey John Brown; Timothy N Mills, all of London, United Kingdom

[73] Assignee: University College London, London, United Kingdom

[21] Appl. No.: 718,448

[22] PCT Filed: Mar. 23, 1995

[86] PCT No.: PCT/GB95/00652

§ 371 Date: Dec. 16, 1996

§ 102(e) Date: Dec. 16, 1996

[87] PCT Pub. No.: WO95/25468

PCT Pub. Date: Sep. 28, 1995

[30] Foreign Application Priority Data

Mar. 23, 1994 [GB] United Kingdom .................. 9405790

[51] Int. Cl.[6] ......................................... A61B 17/06
[52] U.S. Cl. ............................ 606/144; 606/139; 112/169
[58] Field of Search ........................... 606/139, 144, 606/145, 148; 112/169, 80.03

[56] References Cited

U.S. PATENT DOCUMENTS

| 730,152 | 6/1903 | Pitner . |
|---|---|---|
| 2,880,728 | 4/1959 | Rights . |
| 3,013,559 | 12/1961 | Thomas . |
| 3,470,834 | 10/1969 | Bone . |
| 3,470,875 | 10/1969 | Johnson . |
| 4,126,124 | 11/1978 | Miller . |
| 4,144,876 | 3/1979 | DeLeo . |
| 4,164,225 | 8/1979 | Johnson et al. . |
| 4,216,777 | 8/1980 | Pridemore . |
| 4,234,111 | 11/1980 | Dischinger . |
| 4,236,470 | 12/1980 | Stenson . |
| 4,345,601 | 8/1982 | Fukuda . |
| 4,414,908 | 11/1983 | Eguchi et al. . |
| 4,474,174 | 10/1984 | Petruzzi . |
| 4,597,390 | 7/1986 | Muhollan et al. . |
| 4,621,640 | 11/1986 | Mulhollan et al. . |
| 4,741,330 | 5/1988 | Hayhurst . |
| 4,841,888 | 6/1989 | Mills et al. .................. 606/145 |
| 4,890,615 | 1/1990 | Caspari et al. . |
| 4,927,428 | 5/1990 | Richards . |
| 5,037,433 | 8/1991 | Wilk et al. . |
| 5,041,129 | 8/1991 | Hayhurst et al. . |
| 5,100,418 | 3/1992 | Yoon et al. . |
| 5,152,769 | 10/1992 | Baber . |
| 5,211,650 | 5/1993 | Noda . |
| 5,254,126 | 10/1993 | Filipi et al. . |
| 5,281,237 | 1/1994 | Gimpelson . |
| 5,284,485 | 2/1994 | Kammerer et al. . |
| 5,304,184 | 4/1994 | Hathaway et al. . |
| 5,336,229 | 8/1994 | Noda . |
| 5,364,408 | 11/1994 | Gordon . |
| 5,368,601 | 11/1994 | Sauer et al. . |
| 5,389,103 | 2/1995 | Melzer et al. . |
| 5,391,182 | 2/1995 | Chin . |
| 5,403,348 | 4/1995 | Bonutti . |
| 5,405,354 | 4/1995 | Sarrett . |
| 5,417,691 | 5/1995 | Hayhurst . |
| 5,431,666 | 7/1995 | Sauer et al. . |
| 5,433,722 | 7/1995 | Sharpe et al. . |

(List continued on next page.)

FOREIGN PATENT DOCUMENTS

| 2 165 559 | 4/1986 | United Kingdom . |
|---|---|---|
| WO 9609796 | 4/1996 | WIPO . |
| WO 9620647 | 7/1996 | WIPO . |

*Primary Examiner*—Gary Jackson
*Attorney, Agent, or Firm*—Arthur Z. Bookstein; John F. Perullo

[57] ABSTRACT

A sewing device is provided for passing a thread through a substrate portion, particularly a portion of a patient's tissue. The device comprises a hollow needle movable between a first position in which it is out of the substrate portion and a second position in which it passes through the substrate portion. A thread carrier is attached to the thread and can be moved from a position being within the hollow needle to a position outside it.

17 Claims, 7 Drawing Sheets

U.S. PATENT DOCUMENTS

| | | |
|---|---|---|
| 5,437,680 | 8/1995 | Yoon . |
| 5,439,467 | 8/1995 | Benderev et al. . |
| 5,462,558 | 10/1995 | Kolesa et al. . |
| 5,464,426 | 11/1995 | Bonutti . |
| 5,470,337 | 11/1995 | Moss ................................ 606/144 |
| 5,474,573 | 12/1995 | Hatcher . |
| 5,507,754 | 4/1996 | Green et al. . |
| 5,507,758 | 4/1996 | Thomason et al. . |
| 5,520,700 | 5/1996 | Beyar et al. . |
| 5,520,702 | 5/1996 | Sauer et al. . |
| 5,520,703 | 5/1996 | Essig et al. . |
| 5,549,617 | 8/1996 | Green et al. . |
| 5,562,689 | 10/1996 | Green et al. . |
| 5,569,305 | 10/1996 | Bonutti . |
| 5,591,180 | 1/1997 | Hinchliffe ........................ 606/144 |
| B1 4,923,461 | 10/1994 | Caspari et al. . |

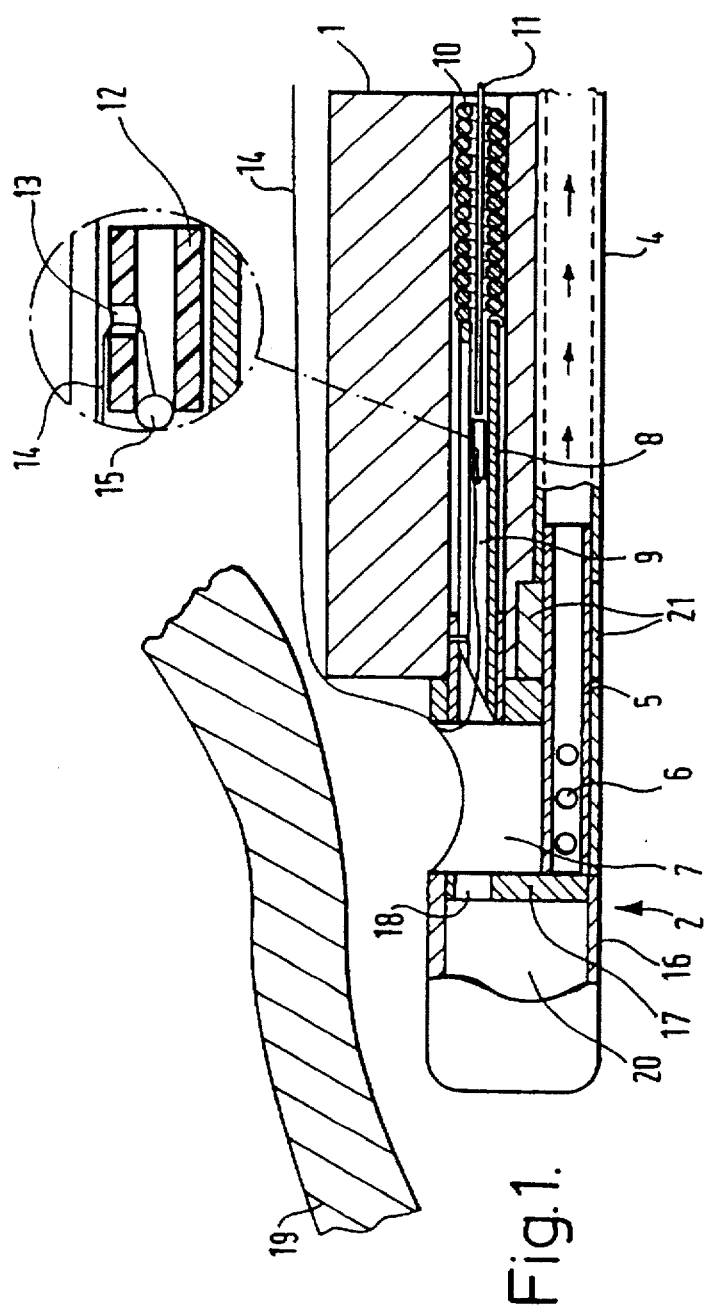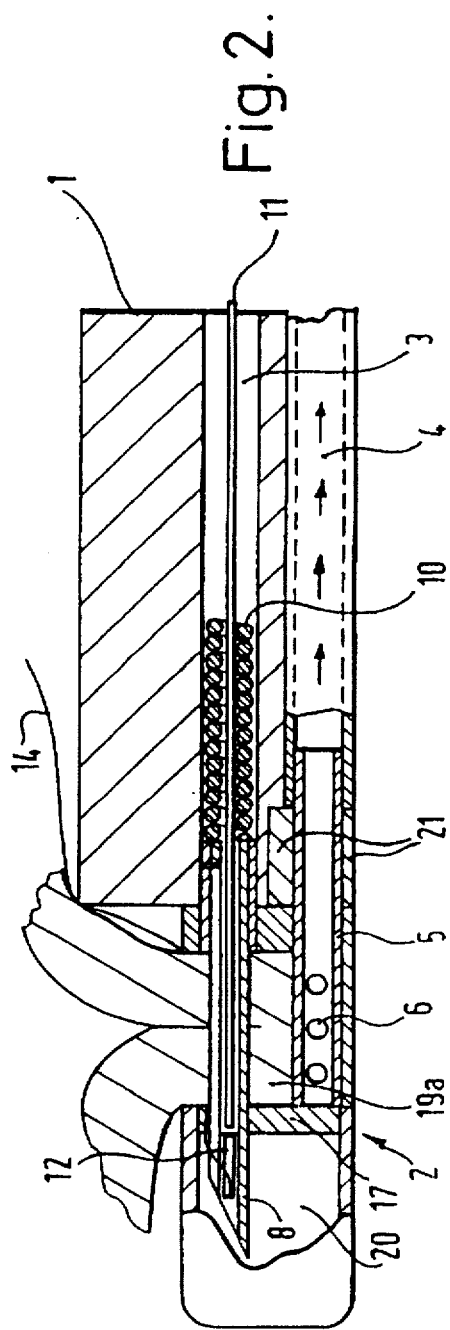

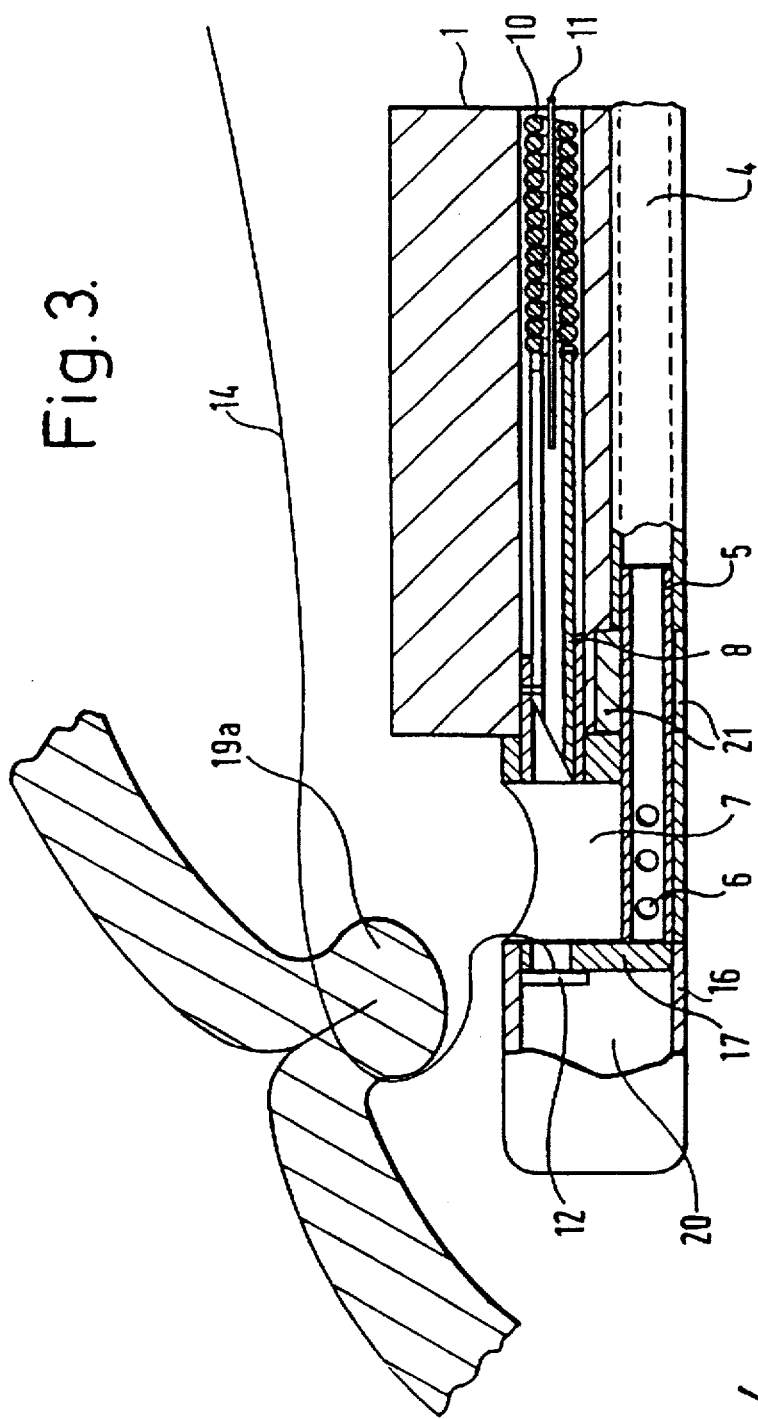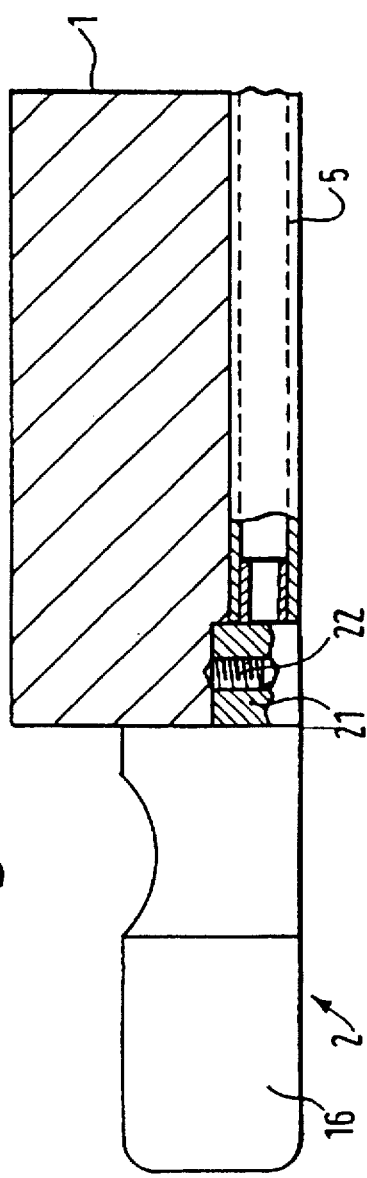

SEWING DEVICE

This invention relates to a sewing device for use in surgical procedures and, more particularly, relates to a device which can be used in the body of a patient without the need to make an external incision in the patient, the device being controlled externally of the patient, for example by endoscopic means. It has particular application to a sewing device for use in flexible endoscopy, though it is also applicable to devices for use in rigid endoscopy.

Sewing devices of this general type are described in, for example, GB-A-2165559 and U.S. Pat. No. 5,080,663. It is an object of the present invention to provide an improved sewing device and, preferably, one which involves a relatively small number of components and can be of small size.

According to the present invention there is provided a sewing device for passing a thread through a substrate portion, which comprises a hollow needle movable between a first position in which it is out of the said substrate portion and a second position in which it passes through the said substrate portion, and a thread carrier adapted to be attached to the said thread and being receivable within the hollow needle.

Preferably, the sewing device comprises a body which defines a cavity within which the substrate portion can be held, for example by means of suction, and the hollow needle is mounted for movement in the body between the said first and second positions.

Two particular embodiments are described below, one of which is a single stitch sewing device, and the other of which is a multiple stitch sewing device. In the single stitch device the thread carrier is transported by the needle through the substrate as the latter passes from its first position to its second position. When the needle returns to its first position, the thread carrier is left behind. In the multiple stitch device, the same procedure occurs, but it is followed by a further step in which the hollow needle travels from its first position to its second position, picks up the thread carrier, and brings it back with it. A second stitch may be formed during this further step, and, in any case, the whole sequence of steps is repeated as many times as may be required to form the desired number of stitches.

The invention will now be further described with reference to the accompanying diagrammatic drawings, in which:

FIGS. 1 to 3 show successive steps in the operation of a single stitch sewing device according to the invention;

FIG. 4 is a view of the device of FIGS. 1 to 3, showing how the sewing device is connected to an endoscope.

Figure 5:
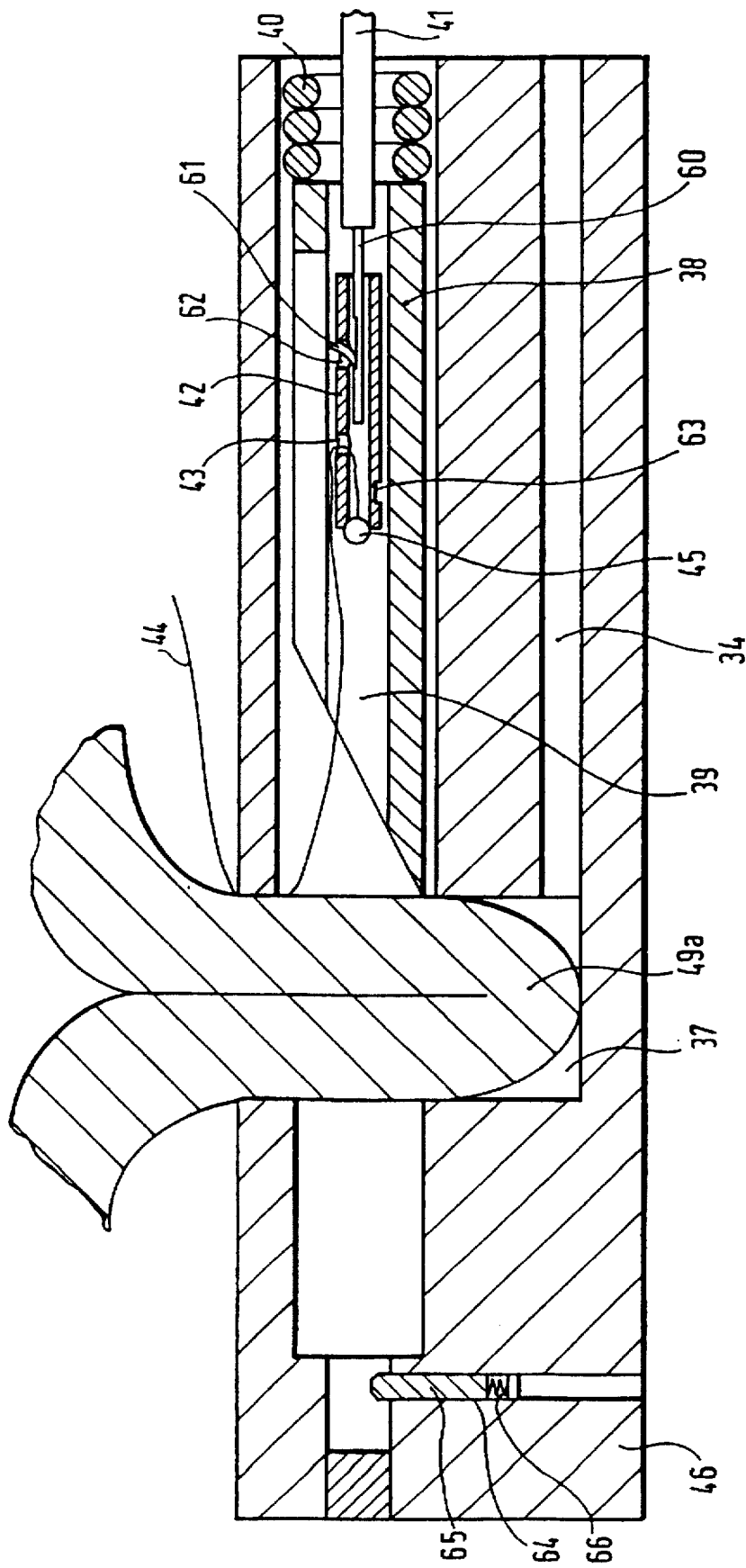
FIGS. 5 to 9 show successive steps in the operation of a multiple stitch sewing device according to the invention.
Figure 6:
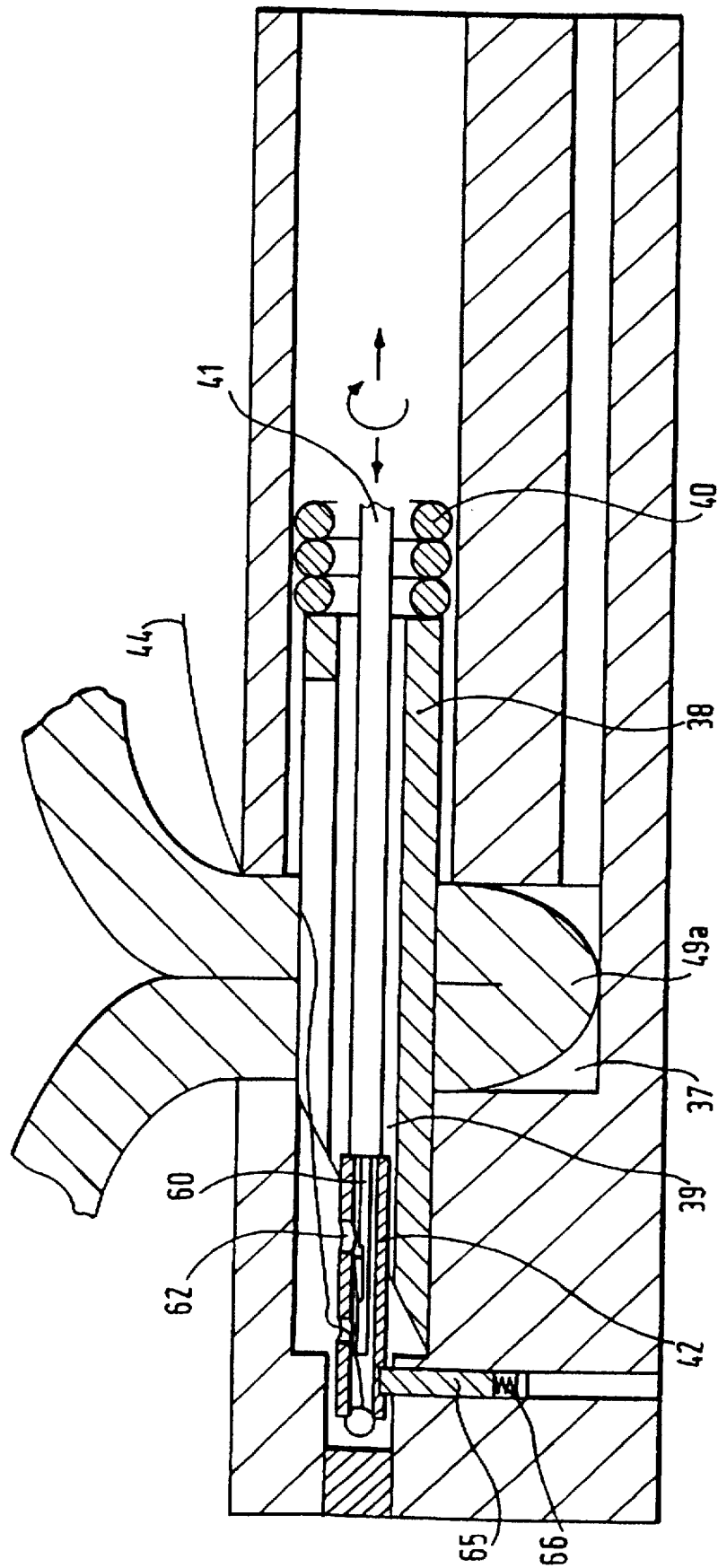

Referring first to FIG. 1, this shows the distal end of a flexible endoscope 1, with a sewing device 2 according to the invention secured thereto. The endoscope is provided with a viewing channel, which is not shown, but which would be in that portion of the endoscope which is on the upper side as seen in the drawings and which would, therefore, have a view in a forward direction substantially unimpeded by the sewing device 2. The endoscope is further provided with a biopsy channel 3, and a suction channel 4 the proximal end of which is connected to a source of reduced pressure (not shown). The use of suction in a flexible endoscope is described in detail in the patent specifications identified above, and attention is directed to those specifications for further details.

The sewing device 2 has a tube 5 which communicates with the suction pipe 4 and has a plurality of perforations 6 therein. These perforations communicate with an upwardly open cavity 7 formed in the sewing device.

A hollow needle 8 is mounted in the biopsy channel 3, with its bevelled tip extending into the sewing device. The needle has a channel 9 extending therethrough. A flexible, wire-wound cable 10 has its forward end attached to the rear of the needle 8, and a centre wire 11 runs within the cable 10, along the entire length thereof, and is longitudinally movable with respect thereto. The diameter of the wire 11 is such that it is longitudinally movable within the channel 9 and, in the position shown in FIG. 1, the forward end portion of the wire 11 extends into the rear end portion of the channel 9.

A thread carrier in the form of a tag 12 is mounted in the channel 9. The tag is shown in more detail in the enlarged scrap view which forms part of FIG. 1, where it can be seen that the tag is hollow (it is in fact in the form of a hollow, plastics cylinder), and has an aperture 13 extending through the side wall thereof. As can also be seen in FIG. 1, one end of a thread 14 is secured to the tag by passing it through the aperture 13 and tying in the end a knot 15 of sufficient size to prevent the thread escaping from the tag.

The sewing device has a hollow head portion 16 defining a chamber 20 therein, with the head portion 16 and the endoscope 1 being on opposite sides of the cavity 7. Between the chamber 20 and the cavity 7 is a wall 17, in which there is formed an aperture 18. The aperture 18 has a diameter which is marginally greater than the external diameter of the needle 8, and is aligned therewith. The clearance between the needle 8 and the aperture 18 must be sufficiently small to prevent tissue being forced through the aperture and causing the needle to jam.

Finally, it is noted that FIG. 1 shows a portion of the patient's tissue 19, being the substrate in which a stitch is to be formed.

In operation, suction is applied to the suction pipe 4, and thence, via the perforations 6 in the tube 5 to the cavity 7. This sucks into the cavity a U-shaped portion 19a of the tissue 19. This is shown in FIG. 2. Then, as also shown in FIG. 2, the hollow needle 8 is pushed through the U-shaped tissue portion 19a, by exerting a leftwards force on the wire-wound cable 10, whereafter the tag 12 is pushed along the channel 9 from right to left, by exerting a leftwards force on the centre wire 11. The end result of these operations is as shown in FIG. 2, where it can be seen that the tip portion of the needle 8 is on the left hand side of the wall 17, within the chamber 20 in the hollow head portion 16, and the tag 12, within the channel 9, lies to the left of the wall 17.

Continued leftwards movement of the wire 11 pushes the tag 12 out of the channel 9 and into the chamber 20. The wire 11 is then withdrawn rightwardly, followed by rightward withdrawal of the cable 10, to bring both back to the positions which they occupy in FIG. 1. The suction is then discontinued, so allowing the U-shaped tissue portion 19a to be released from the cavity 7. The position is then as shown in FIG. 3. Finally, the endoscope and sewing device are withdrawn from the patient. In so doing, the thread 14 is pulled partially through the tissue portion 19a, since the tag 12 is trapped in the chamber 20. The end result is that both ends of the thread are outside of the patient and can be knotted and/or severed as may be appropriate.

FIG. 4 shows that the sewing device 2 is connected to the endoscope 1 by a U-shaped collar 21 (also visible in FIGS. 1 to 3) and a pair of socket set screws 22. Although this cannot be seen in the drawings, the arms of the collar extend part way up the respective sides of the endoscope 1.

The embodiment shown in FIGS. 1 to 4 is intended to form a single stitch in the patient's tissue. To form more than one stitch it is necessary after each is formed to withdraw the endoscope with the sewing device thereon, reload it, and then reinsert it in the patient. The embodiment of FIGS. 5 to 9 is intended to form a plurality of stitches in a patient's tissue without the need to remove and reinsert the device in the patient, and constitutes a chain stitch sewing device. Where there are features in this embodiment which correspond in substance to features in the first embodiment, reference numerals are used which correspond to those of the first embodiment, but increased by 30.

In the embodiment of FIGS. 5 to 9, the wire 41 carries a needle 60 at its distal end, and this wire is provided with a resilient barb 61 which, in the absence of a force thereon, extends outwardly from the needle. The thread carrier 42 has an additional aperture 62 and, in the position shown in FIG. 5, the barb 61 extends into this aperture. A recess 63 is provided on the lower surface of the thread carrier, adjacent the distal end thereof.

The head portion 46 has a bore 64 in which a catch member 65 is slidably mounted. The catch member biased in an upward direction by a compression spring 66 which bears on the lower end thereof. The catch member 65 thus normally extends outwardly from the bore 64, as illustrated in FIG. 5.

In use of the device of FIGS. 5 to 9, suction is applied to channel 34 to draw into the cavity 37 a U-shaped tissue portion 49a. The situation is as shown in FIG. 5. The needle 38 is then pushed through the tissue portion 49a by exerting a force on the cable 40, whereafter the wire 41 is pushed leftwardly. In performing the latter operation the barb 61 becomes depressed to allow the pin 60 to move leftwardly within the thread carrier 42 until the distal end of the wire 41 engages the proximal end of the thread carrier. Further movement of the wire causes it to move the thread carrier leftwardly, through the passage 39 in the needle 38, until the catch member 65 engages in the recess 63. The wire 41 is then twisted about its own longitudinal axis through less than a complete revolution, for example through an angle of 90°, so that the barb 61 is no longer longitudinally aligned with the aperture 62. The device is then in the situation shown in FIG. 6.

Figure 7:
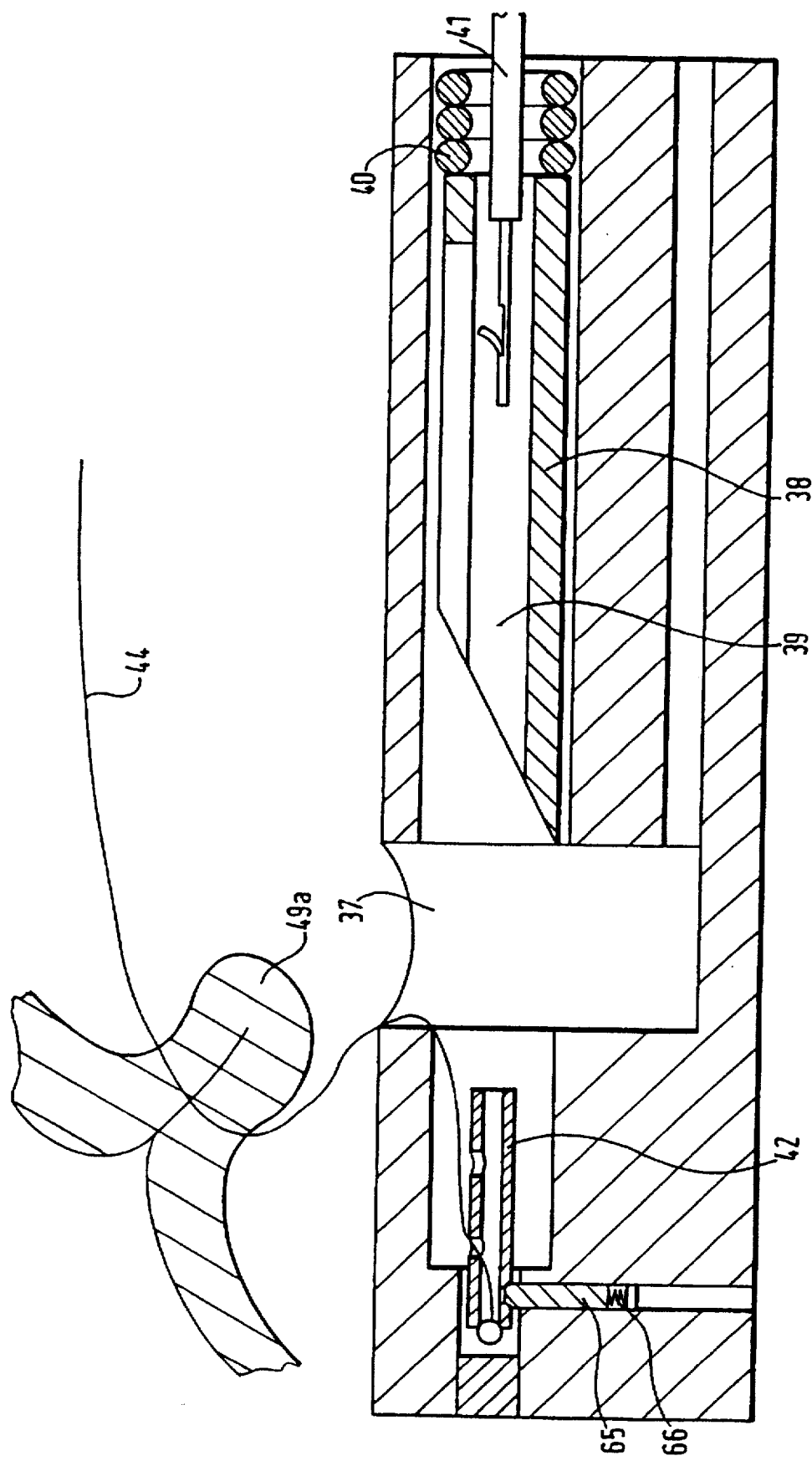

Next, the wire 41 is withdrawn rightwardly through the channel 39, until it reaches the position which it is shown as occupying in FIG. 7, and the needle is withdrawn rightwardly, also to the position shown in FIG. 7. The thread carrier 42 remains on the left hand side of the cavity 37, caught by the catch member 65. The suction is then discontinued, allowing the tissue portion 49a to be released from the cavity 37. The device is then in the condition shown in FIG. 7. At this point, one stitch has been formed in the tissue.

Figure 8:
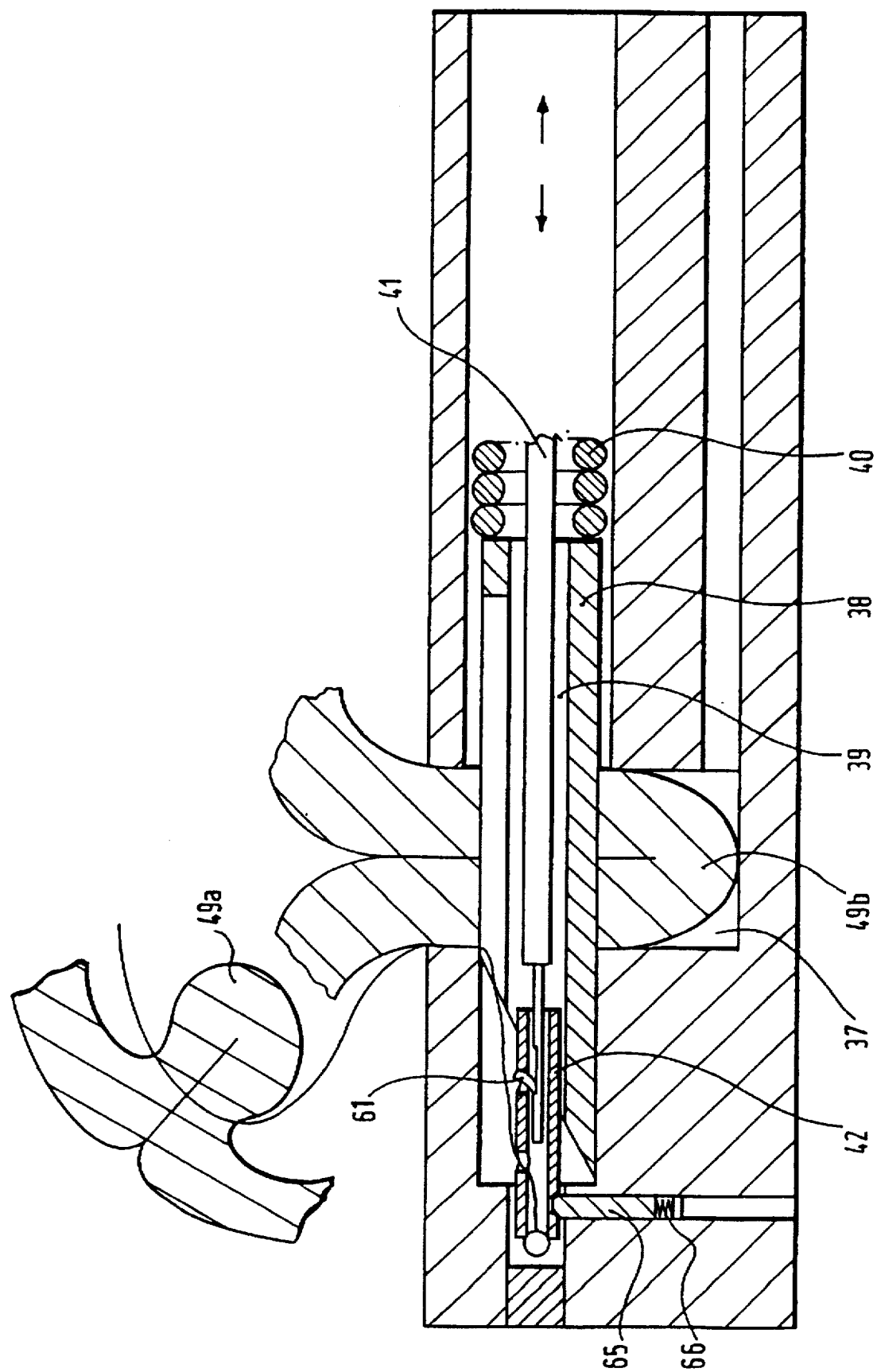

The sewing device is then repositioned so that the cavity 37 is adjacent that part of the patient's tissue where the next stitch is to be formed, and suction is reapplied to draw into the cavity 37 a further tissue portion, denoted in FIG. 8 by reference numeral 49b. The needle 38 is then moved leftwardly, through the tissue portion 49b, following which the wire 41 is also moved leftwardly, through the channel 39. Either before or after the wire 41 is moved leftwardly, it is rotated about its own longitudinal axis to line up the barb 61 with the aperture 62, so that the barb once again engages with the aperture. The device is then in the condition shown in FIG. 8.

Figure 9:
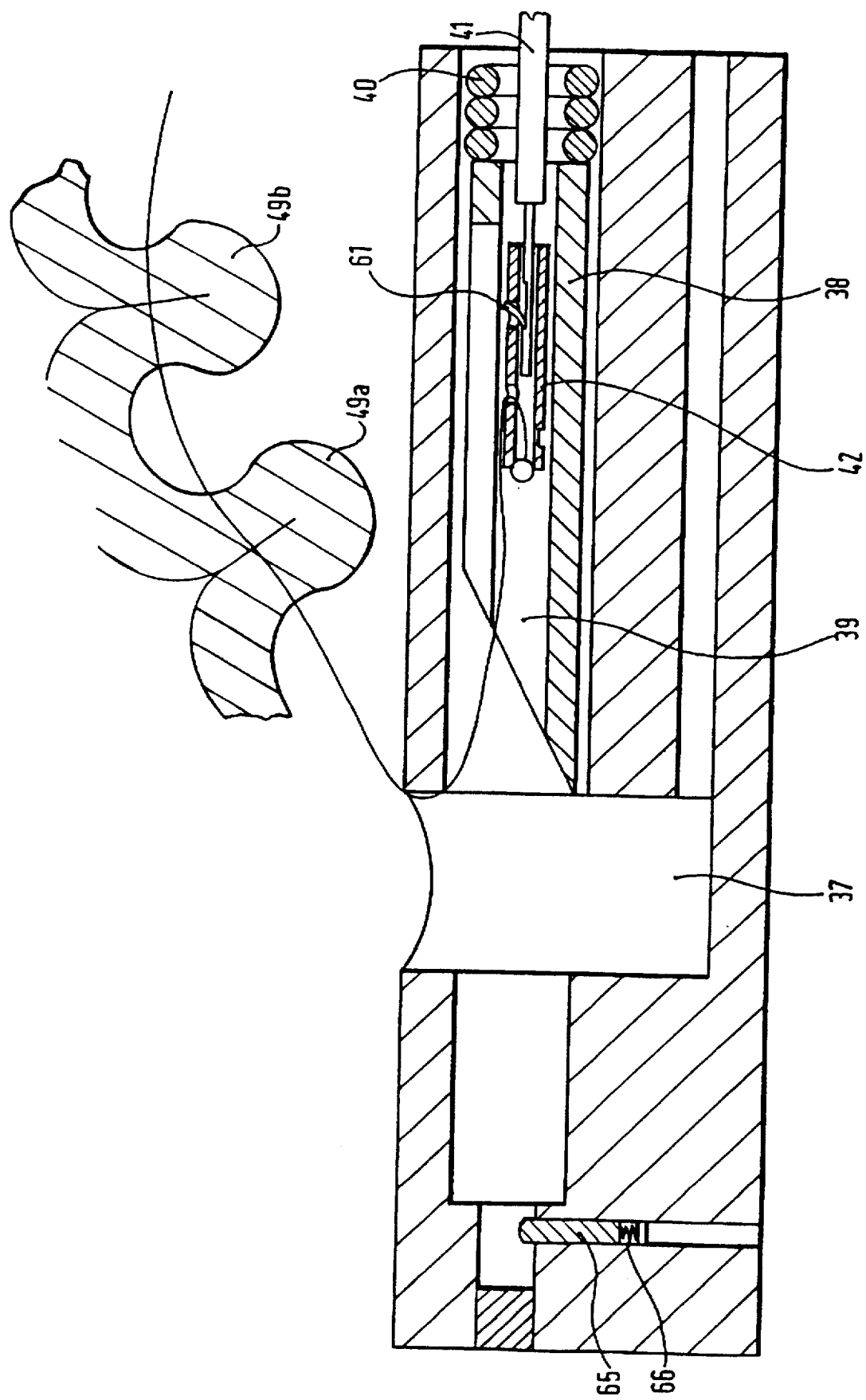

The compression spring 66 is chosen so that it only applies a low force to the catch member 65, and when the wire 41 is then moved rightwardly, the force which the barb 61 exerts on the thread carrier 42 is sufficient to overcome the retaining force exerted on the thread carrier by the catch member. Once the wire 41 and thread carrier 42 are back in their rightward position, the needle 38 is moved rightwards and the suction is discontinued, permitting the tissue portion 49b to be released from the cavity 37. The situation is then as shown in FIG. 9, at which point it can be seen that two stitches have been formed.

The above process is repeated as many times as is necessary to form the required number of stitches. As a modification thereof, stitches could be formed either only when the needle and thread carrier move from right to left or only when the needle and thread carrier move from left to right. During the movement when no thread was to be formed, no suction would be applied to draw a tissue portion into the cavity 37. Also, the procedure in which threads are formed during movement in both directions will form an even number of stitches, and if an odd number of stitches is to be formed no stitch must be made during an odd number of needle and thread carrier movements.

In the above described embodiment, a mechanical means, namely the interengagement of a barb and an aperture, is used to provide a releasable connection between the thread carrier and the member (wire 41) which moves it. An alternative possibility would be to use an electromagnetic connection between the two, which could then be switched on and off as desired.

We claim:

1. A sewing device for passing a thread through a tissue substrate portion, which comprises a hollow needle movable between a first position on one side of the substrate portion in which it is out of the substrate portion and a second position in which it passes through the substrate portion and toward a portion of the sewing device on a through side of the substrate, and a capturable thread carrier attached to the thread and receivable within the hollow needle such that the carrier can be passed through the substrate by the needle and become captured by the portion of the sewing device on the through side of the substrate.

2. A device according to claim 1, further comprising an open cavity for receiving the said substrate portion.

3. A device according to claim 2, further comprising at least one suction port arranged to apply suction to the substrate portion to draw the same into the cavity.

4. A device according to claim 2, wherein when the needle is in the said first position a leading end thereof is located proximally of the cavity, and when the needle is in the said second position the leading end thereof is located distally of the said cavity.

5. A device according to claim 4, wherein a chamber is provided on the distal side of the cavity, the chamber communicating with the cavity via an aperture of a size sufficient to allow the leading end of the needle to pass therethrough.

6. A device according to claim 5, wherein the thread carrier is so dimensioned that it is passable through the aperture when carried within the needle yet when ejected into the chamber with the thread attached thereto and passing outwardly through the said aperture and through the substrate portion, the orientation and size of the carrier prevent its withdrawal through the aperture by pulling the thread.

7. A device according to claim 5, further comprising a first elongate member configured to move the needle from its first position to its second position, and vice versa, and a second elongate member configured to move the thread carrier from a position within the needle to a position exterior thereof.

8. A device according to claim 7, wherein the said second elongate member is slidable within the first elongate member.

9. A device according to claim 2, comprising a first elongate member configured to move the needle from its first position to its second position, and vice versa, and a second elongate member configured to move the thread carrier from a position within the needle to a position exterior thereof, the said second elongate member and the thread carrier being provided with a connector providing a releasable connection therebetween.

10. A device according to claim 9, wherein the thread carrier has a hollow interior and the second elongate member has a portion adapted to be releasably held within the hollow interior.

11. A device according to claim 10, wherein the connector comprises a barb on the exterior of the said thread carrier portion, and a recess in the thread carrier with which the barb is engageable.

12. A device according to claim 11, wherein the barb is releasable from the thread carrier by rotation of the said second means about the longitudinal axis thereof.

13. A device according to claim 9, which is provided distally of the said cavity with a catch for releasably holding the thread carrier.

14. A device according to claim 13, wherein the catch is a mechanical member.

15. A device according to claim 14, wherein the mechanical member is spring-biassed into engagement with a recess in the exterior wall of the thread carrier.

16. A device according to claim 13, wherein the catch is electromagnetic in operation.

17. A method for suturing tissue endoscopically comprising:

providing a sewing device for passing a thread through a tissue substrate portion, which comprises a hollow needle movable between a first position in which it is out of the tissue substrate portion and a second position in which it passes through the substrate portion and toward a portion of the sewing device on a through side of the tissue substrate, and a capturable thread carrier attached to the thread and receivable within the hollow needle such that the carrier can be passed through the substrate by the needle and become captured by the portion of the sewing device on the through side of the substrate;

disposing the sewing device at the distal end of an endoscope;

inserting the endoscope into the patient and positioning the sewing device adjacent to tissue to be sutured;

passing the needle and thread carrier through the tissue;

ejecting the thread carrier from the needle;

capturing the thread carrier in position on the through side of the tissue;

withdrawing the needle from the tissue;

withdrawing the thread carrier and sewing device from the tissue to draw the thread through the tissue.

* * * * *